(12) United States Patent
Bunnage et al.

(10) Patent No.: US 6,730,786 B2
(45) Date of Patent: May 4, 2004

(54) PROCESS FOR THE PREPARATION OF PYRAZOLOPYRIMIDINONES

(75) Inventors: Mark Edward Bunnage, County of Kent (GB); Philip Charles Levett, County of Kent (GB); Nicholas Murray Thomson, County of Kent (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/886,643

(22) Filed: Jun. 21, 2001

(65) Prior Publication Data

US 2002/0013465 A1 Jan. 31, 2002

Related U.S. Application Data

(60) Provisional application No. 60/217,794, filed on Jul. 12, 2000, and provisional application No. 60/291,026, filed on May 16, 2001.

(30) Foreign Application Priority Data

Jun. 22, 2000 (GB) .............................................. 0015462
Mar. 9, 2001 (GB) .............................................. 0105878

(51) Int. Cl.[7] ........................................... C07D 487/04
(52) U.S. Cl. ..................................... 544/256
(58) Field of Search ......................... 544/256

(56) References Cited

FOREIGN PATENT DOCUMENTS

| | | | |
|---|---|---|---|
| DE | 2444720 | 9/1974 | ......... C07C/143/78 |
| DE | 2444720 | 4/1975 | ......... C07C/143/78 |
| EP | 0463756 | 1/1992 | ......... C07D/487/04 |
| EP | 0812845 | 12/1997 | ......... C07D/487/04 |
| EP | 0916675 | 5/1999 | ......... C07D/487/04 |
| WO | WO9428902 | 12/1994 | ......... A61K/31/505 |
| WO | WO9954333 | 12/1998 | ........... C12N/15/57 |
| WO | WO9964004 | 12/1999 | ......... A61K/31/505 |
| WO | WO0024745 | 5/2000 | ......... C07D/487/04 |
| WO | WO 0122918 | 4/2001 | |
| WO | WO0122918 | 4/2001 | |

OTHER PUBLICATIONS

D. P. Rotella et al., Journal of Medicinal Chemistry, vol. 43, No. 7, Apr. 6, 2000, pp. 1257–1263 XP002174403.
D. P. Rotella et al., Journal of Medicinal Chemistry, vol. 43, No. 26, Dec. 28, 2000, pp. 5037–5043 XP002174404.

*Primary Examiner*—John M. Ford
(74) *Attorney, Agent, or Firm*—Peter C. Richardson; Gregg C. Benson; James T. Jones

(57) ABSTRACT

There is provided a process for the production a compound of general formula I:

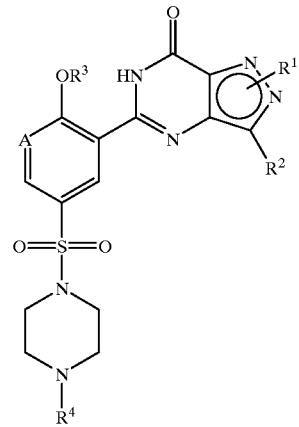

wherein A, $R^1$, $R^2$, $R^3$ and $R^4$ have meanings given in the description, which process comprises the dehydrogenation of a compound of general formula II,

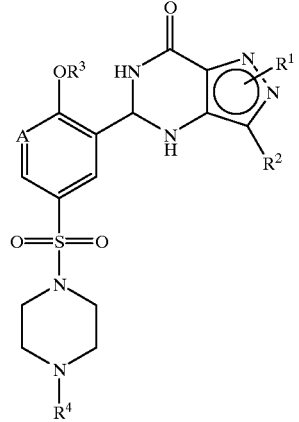

16 Claims, No Drawings

PROCESS FOR THE PREPARATION OF PYRAZOLOPYRIMIDINONES

This application is filed claiming priority from co-pending Provisional Application Nos. 60/217,794 filed Jul. 12, 2000 and 60/291,026 filed May 16, 2001.

This invention relates to a novel process for the production of 4-alkylpiperazinylsulfonylphenyl- and 4-alkylpiperazinylsulfonyl pyridinyldihydropyrazolo[4,3-d]pyrimidin-7-one derivatives, and, in particular, the anti-impotence drug, sildenafil and analogues thereof.

Sildenafil (5-[2-ethoxy-5-(4-methylpiperazin-1-ylsulfonyl)phenyl]-1-methyl-3-n-propyl-1,6-dihydro-7H-pyrazolo[4,3-d]pyrimidin-7-one),

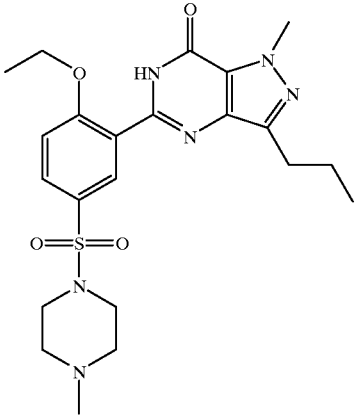

is the active ingredient in Viagra™. The compound, which was originally disclosed in European patent application EP 463 756, has been found to be particularly useful in the treatment of inter alia male erectile dysfunction (see international patent application WO 94/28902).

Multi-step syntheses for the production of sildenafil are described in EP 463 756. An improved process for its production is described in a later application (European patent application EP 812 845), the final step of which involves an internal cyclisation under basic, neutral or acidic conditions.

We have now found that sildenafil and analogues thereof may be made via a novel process, as described hereinafter, which process has advantages over the processes described in the above-mentioned prior art documents.

According to a first aspect of the invention, there is provided a process for the production of compounds of general formula I:

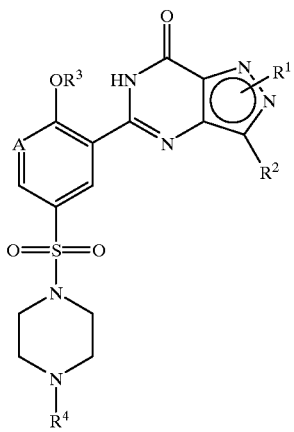

wherein

A represents CH or N;
R$^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, OR$^5$, C(O)R$^6$, C(O)OR$^7$, C(O)NR$^8$R$^9$, NR$^{10a}$R$^{10b}$ and SO$_2$NR$^{11a}$R$^{11b}$;
R$^2$ and R$^4$ independently represent lower alkyl;
R$^3$ represents lower alkyl, which alkyl group is optionally interrupted by oxygen;
Het represents an optionally substituted four- to twelve-membered heterocyclic group, which group contains one or more heteroatoms selected from nitrogen, oxygen and sulfur;
R$^5$, R$^6$, R$^7$, R$^8$, R$^9$, R$^{11a}$ and R$^{11b}$ independently represent H or lower alkyl;
R$^{10a}$ and R$^{10b}$ either independently represent, H or lower alkyl or, together with the nitrogen atom to which they are attached, represent azetidinyl, pyrollidinyl or piperidinyl,
which process comprises the dehydrogenation of a compound of general formula II,

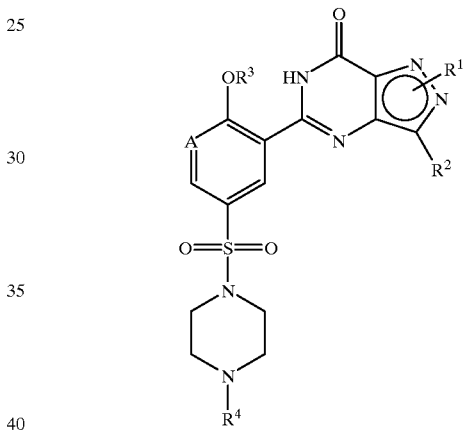

wherein A, R$^1$, R$^2$, R$^3$ and R$^4$ are as defined above, which process is referred to hereinafter as "the process of the invention".

According to a second aspect of the invention, there is provided a process for the production of compounds of general formula I:

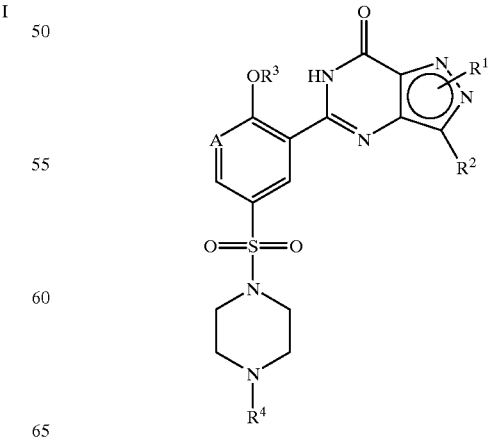

wherein

A represents CH or N;

$R^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^2$ and $R^4$ independently represent lower alkyl;

$R^3$ represents lower alkyl, which alkyl group is optionally interrupted by oxygen; Het represents an optionally substituted four- to twelve-membered heterocyclic group, which group contains one or more heteroatoms selected from nitrogen, oxygen and sulfur;

$R^5$, $R^6$, $R^7$, $R^8$, $R^9$, $R^{11a}$ and $R^{11b}$ independently represent H or lower alkyl;

$R^{10a}$ and $R^{10b}$ either independently represent, H or lower alkyl or, together with the nitrogen atom to which they are attached, represent azetidinyl, pyrollidinyl or piperidinyl;

with the proviso that the compound of formula I is not sildenafil;

which process comprises the dehydrogenation of a compound of general formula II,

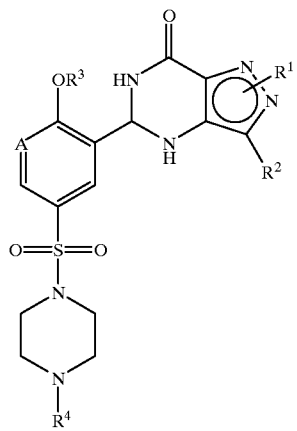

II wherein A, $R^1$, $R^2$, $R^3$ and $R^4$ are as defined above, which process is referred to hereinafter as "the process of the invention".

According to a third aspect of the invention, there is provided a process for the production of compounds of general formula I:

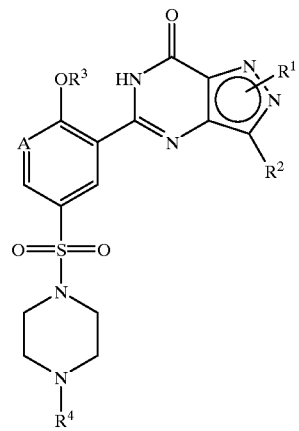

I wherein
A represents CH;

$R^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^2$ and $R^4$ independently represent lower alkyl;

$R^3$ represents lower alkyl, which alkyl group is optionally interrupted by oxygen;

Het represents an optionally substituted four- to twelve-membered heterocyclic group, which group contains one or more heteroatoms selected from nitrogen, oxygen and sulfur;

$R^5$, $R^6$, $R^7$, $R^8$, $R^9$, $R^{11a}$ and $R^{11b}$ independently represent H or lower alkyl;

$R^{10a}$ and $R^{10b}$ either independently represent, H or lower alkyl or, together with the nitrogen atom to which they are attached, represent azetidinyl, pyrollidinyl or piperidinyl;

with the proviso that the compound of formula I is not sildenafil;

which process comprises the dehydrogenation of a compound of general formula II,

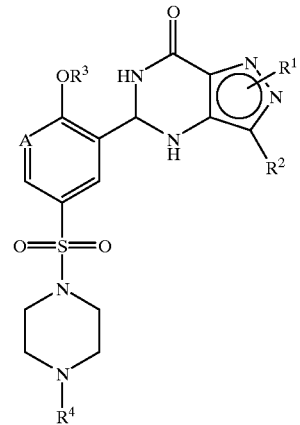

II wherein A, $R^1$, $R^2$, $R^3$ and $R^4$ are as defined above, which process is referred to hereinafter as "the process of the invention".

According to a fourth aspect of the invention, there is provided a process for the production of compounds of general formula I:

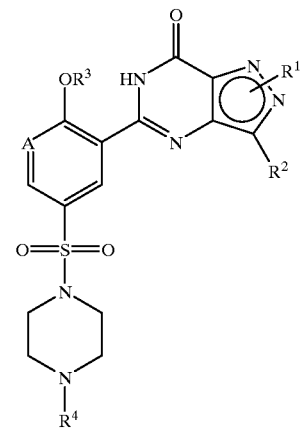

I wherein
A represents N;

$R^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^2$ and $R^4$ independently represent lower alkyl;

$R^3$ represents lower alkyl, which alkyl group is optionally interrupted by oxygen;

Het represents an optionally substituted four- to twelve-membered heterocyclic group, which group contains one or more heteroatoms selected from nitrogen, oxygen and sulfur;

$R^5$, $R^6$, $R^7$, $R^8$, $R^9$, $R^{11a}$ and $R^{11b}$ independently represent H or lower alkyl;

$R^{10a}$ and $R^{10b}$ either independently represent, H or lower alkyl or, together with the nitrogen atom to which they are attached, represent azetidinyl, pyrollidinyl or piperidinyl, which process comprises the dehydrogenation of a compound of general formula II,

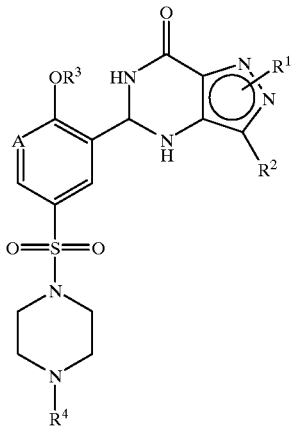

II wherein A, $R^1$, $R^2$, $R^3$ and $R^4$ are as defined above, which process is referred to hereinafter as "the process of the invention".

The compounds of general formulae I and II can be represented by the formulae IA and IB and IIA and IIB as detailed hereinafter. The novel process according to the present invention includes compounds of the formulae IA, IB, IIA and IIB.

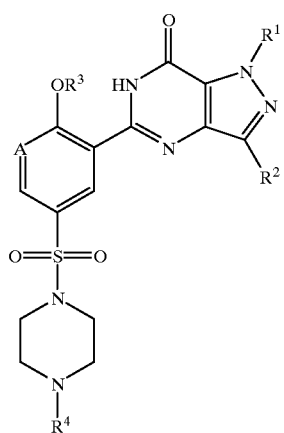

IA

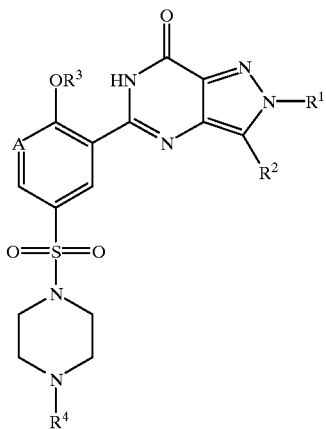

IB

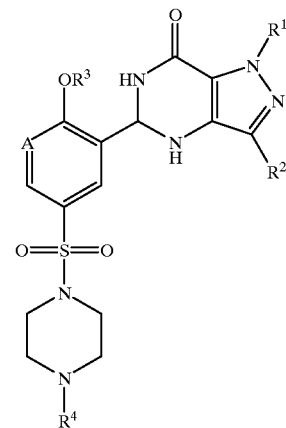

IIA

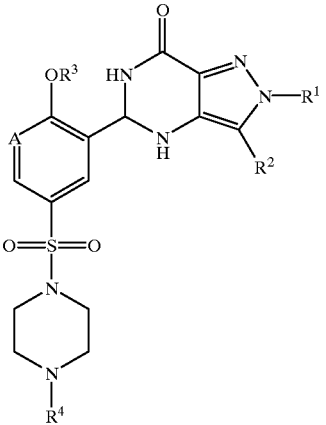

IIB

The term "aryl", when used herein, includes six- to ten-membered carbocyclic aromatic groups, such as phenyl and naphthyl and the like.

Het groups may be fully saturated, partly unsaturated, wholly aromatic, partly aromatic and/or bicyclic in character. Het groups that may be mentioned include groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl, piperazinyl, thienyl and furanyl.

The point of attachment of any Het group may be via any atom in the ring system including (where appropriate) a heteroatom. Het groups may also be present in the N- or S-oxidised form.

The term "lower alkyl" (which includes the alkyl part of alkylHet and alkylaryl groups), when used herein, includes $C_{1-6}$ alkyl (e.g. $C_{1-4}$ alkyl). Unless otherwise specified, alkyl groups may, when there is a sufficient number of carbon atoms, be linear or branched, be saturated or unsaturated, be cyclic, acyclic or part cyclic/acyclic, and/or be substituted by one or more halo atoms.

As defined herein, the term "halo" includes fluoro, chloro, bromo and iodo.

Compounds of formulae I, IA and IB may contain one or more asymmetric carbon atoms and may therefore exhibit optical and/or diastereoisomerism. The process of the invention thus also relates to the formation of stereoisomers of compounds of formulae I, IA and IB and mixtures thereof. Stereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, crystallisation, chromatography over silica or, for example, via classical resolution with a homochiral acid salt). The formation of all stereoisomers is included within the scope of the invention.

Preferred compounds of formulae I, IA and IB include those in which:

$R^1$ represents $C_{1-4}$ alkyl, which alkyl group is optionally interrupted by an oxygen atom, and/or is optionally terminated by a Het group (such as a pyridinyl group);
$R^2$ represents $C_{1-4}$ alkyl;
$R^3$ represents $C_{1-5}$ alkyl, which alkyl group is optionally interrupted by an oxygen atom;
$R^4$ represents $C_{1-3}$ alkyl.

More preferred compounds of formulae I, IA and IB include those in which:

$R^1$ represents linear $C_{1-3}$ alkyl, which alkyl group is optionally interrupted by an oxygen atom, or is optionally terminated by a 2-pyridinyl group (e.g. to form a 2-pyridinylmethyl group);
$R^2$ represents linear $C_{2-3}$ alkyl;
$R^3$ represents linear or branched $C_{2-4}$ alkyl, which alkyl group is optionally interrupted by an oxygen atom;
$R^4$ represents $C_{1-2}$ alkyl.

Particularly preferred compounds that may be formed in the process of the invention include sildenafil, and the following four compounds:

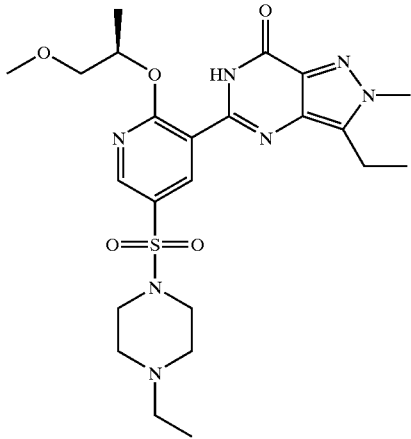

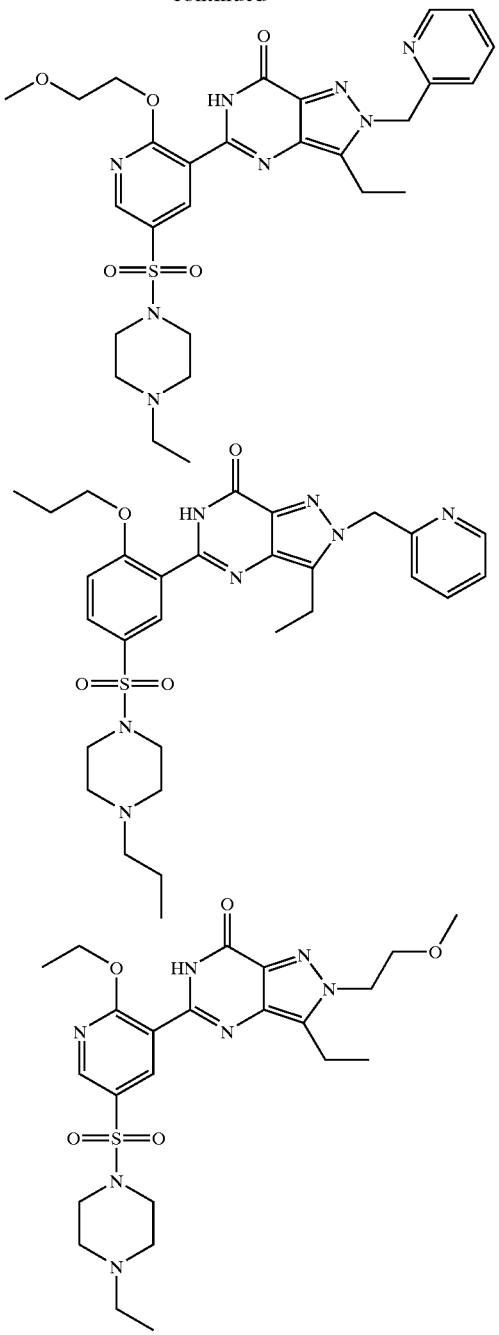

The process of the invention may be carried out in accordance with reaction conditions known to those skilled in the art in the presence of a suitable dehydrogenation agent (for example: a catalyst such as palladium on carbon (e.g. 5% Pd/C or 10% Pd/C), preferably in the presence of a hydrogen acceptor such as cyclohexene or maleic acid and/or an acid such as trifluoroacetic acid, HCl or $H_2SO_4$; a high oxidation potential quinone such as 2,3,5,6-tetrachloro-1,4-benzoquinone or 2,3-dichloro-5,6-dicyano-1,4-benzoquinone; (atmospheric) oxygen; $MnO_2$; or triphenylmethanol in trifluoroacetic acid). A hydrogen sulfite salt such as sodium hydrogen sulfite may also serve to effect removal of hydrogen from the compound of general formula II (IIA and IIB). Preferred dehydrogenation agents include catalysts such as 5% Pd/C or 10% Pd/C, preferably in the presence of a hydrogen acceptor such as cyclohexene or maleic acid and/or an acid such as trifluoroacetic acid. The reaction may be carried out in an appropriate organic solvent system, which solvent system should not significantly react chemically with, or significantly give rise to stereochemical changes in, the reactants or product once formed, or significantly give rise to other side reactions. Preferred solvent systems include aromatic hydrocarbons, such toluene and xylene.

The process of the invention may be carried at above room temperature (e.g. between 125 and 250° C., preferably 150 and 230° C., more preferably 175 and 220° C., depending upon the solvent system that is employed), and/or at high pressure (e.g. between 13.8 and 68.9 kPa (2 and 10 psi), preferably between 27.6 and 41.4 kPa (4 and 6 psi), such as around 34.5 kPa (5 psi)), and/or, optionally, in an inert atmosphere (i.e. in the presence of an inert gas, such as nitrogen or argon).

Appropriate reaction times and reaction temperatures depend upon the solvent system that is employed, as well as the compound that is to be formed, but these may be determined routinely by the skilled person.

We have found that compounds of general formula II (and IIA and IIB) hereinbefore defined may be prepared, advantageously, by way of reaction of an aldehyde compound of formula III,

III

[Chemical structure of formula III: aromatic ring A with $OR^3$ substituent, CHO group, and $SO_2$-piperazine-$R^4$ group]

wherein A, $R^3$ and $R^4$ are as hereinbefore defined, with a compound of formula IV,

IV

[Chemical structure of formula IV: pyrazole with $H_2N$-C(O)-, $H_2N$-, $R^1$, $R^2$ substituents]

wherein $R^1$ and $R^2$ are as hereinbefore defined.

This condensation/cyclisation reaction may be carried out at above room temperature (e.g. at around the reflux temperature of the solvent that is employed) in the presence of a suitable solvent (for example: an aromatic hydrocarbon, such as toluene or xylene; chlorobenzene; or diphenylether). This reaction may also be carried out under pressure at a higher temperature than the reflux temperature of the relevant solvent that is employed.

The compounds of general formula IV may be represented by the formulae IVA and IVB.

IVA

[Chemical structure of formula IVA]

IVB

[Chemical structure of formula IVB]

Advantageously, we have found that compounds of general formula I (and IA and IB) hereinbefore defined may be formed directly from corresponding compounds of formula III in a "one pot" procedure, in which a compound of formula III is reacted with a compound of general formula IV at high temperature, and under pressure, using an appropriate reaction vessel. Following this reaction, the dehydrogenation agent(s) may be added to the reaction vessel and the dehydrogenation reaction performed on the intermediate compound of formula IIA or IIB, formed in situ, under similar conditions to those described hereinbefore.

Without wishing to be bound by a particular theory, it is believed that the reaction between compounds III and IV proceeds via either an imine intermediate of general structure:

[Chemical structure: imine intermediate]

imine intermediate or an aminol intermediateof general structure:

[Chemical structure: aminol intermediate]

aminol intermediate to form the compound of general formula II as hereinbefore defined.

Compounds of formula III may be prepared by known techniques. For example:

(a) Compounds of formula III in which A represents CH may be prepared from readily available starting materials of formula V,

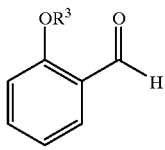

V wherein $R^3$ is as hereinbefore defined, in analogous fashion to the techniques described in German patent application DE 24 44 720, the disclosure in which document is hereby incorporated by reference.

(b) Compounds of formula III in which A represents CH may alternatively be prepared by oxidation of a compound of formula VI,

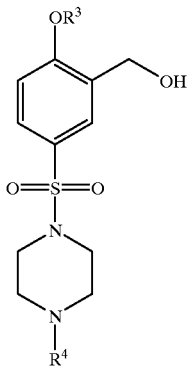

VI wherein $R^3$ and $R^4$ are as hereinbefore defined, in the presence of a suitable oxidising agent (for example: $MnO_2$; tetra-n-propylammonium perruthenate (catalytic) combined with 4-methylmorpholine N-oxide; or oxalyl chloride combined with dimethylsulfoxide and triethylamine) and an appropriate organic solvent (for example: acetone; dichloromethane; an aromatic hydrocarbon (e.g. toluene or xylene); chlorobenzene; or an aliphatic hydrocarbon (e.g. pentane, hexane or petroleum ether)).

Compounds of formula VI may be prepared directly by reduction of a corresponding carboxylic acid of formula VII,

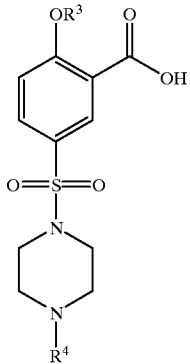

VII wherein $R^3$ and $R^4$ are as hereinbefore defined, under conditions known to those skilled in the art (for example, using: $LiAlH_4$; borane; $NaBH_4$, added after activation with iodine; diisobutylaluminium hydride; or $NaBH_4$ combined with an acid activating agent (e.g. carbonyldiimidazole, thionyl chloride or methyl chloroformate)). Compounds of formula VII may be prepared according to, or by analogy with, methods described in European patent application EP 812 845.

However, in order to prepare compounds of formula VI more conveniently, we prefer that a compound of formula VII is first esterified under standard conditions to form a compound of formula VIIIA,

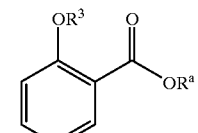
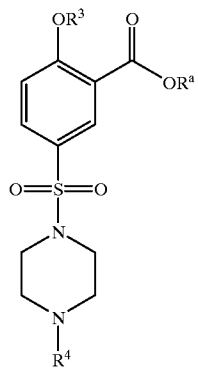

VIIIA wherein $R^a$ represents lower alkyl (e.g. $C_{1-6}$, such as linear or branched $C_{1-4}$, alkyl (e.g. methyl, ethyl or n- or i-propyl)) and $R^3$ and $R^4$ are as hereinbefore defined, followed by reduction of the ester using techniques known to those skilled in the art (e.g. catalytic hydrogenation or, more preferably, chemical reduction). Appropriate chemical reducing agents include, for example, Red-Al®, DIBAL-H or $LiAlH_4$. When the reducing agent is, for example, Red-Al®, the reduction may be carried out in the presence of a suitable organic solvent (for example: an aromatic hydrocarbon (e.g. toluene or xylene); chlorobenzene; an aliphatic hydrocarbon (e.g. pentane, hexane or petroleum ether); THF; diisopropyl ether; or dichloromethane), under a positive pressure of inert gas (e.g. nitrogen or argon), for example at or around room temperature.

(c) Compounds of formula III in which A represents N may be prepared by reduction of a corresponding compound of formula VIIIB,

VIIIB wherein $R^a$, $R^3$ and $R^4$ are as hereinbefore defined, in the presence of a suitable reducing agent, for example, Red-Al® or DIBAL-H. When the reducing agent is DIBAL-H, this reduction may be performed, for example, at low temperature (e.g. at −78° C.) in the presence of an appropriate solvent (for example: an aromatic hydrocarbon (e.g. toluene or xylene); chlorobenzene; an aliphatic hydrocarbon (e.g. pentane, hexane or petroleum ether); THF; diisopropyl ether; or dichloromethane).

Preferred compounds of formula III include those in which A represents N.

Compounds of formula VIIIB may be prepared in accordance with the methods detailed in the preparation section herein and by known techniques. For example, compounds of formula VIIIB may be prepared according to or by analogy with the procedures described in WO 99/54333 (in particular the procedures described in Preparations 18 and 19 of that document), the disclosures in which document are hereby incorporated by reference.

Compounds of formulae IV and V, and derivatives thereof, when not commercially available or not subsequently described, may be obtained by conventional synthetic procedures or by analogy with the processes described herein, in accordance with standard techniques, from readily available starting materials using appropriate reagents and reaction conditions.

Compounds may be isolated from reaction mixtures using known techniques.

Substituents on the aryl (e.g. phenyl), and (if appropriate) heterocyclic, group(s) in compounds defined herein may be converted to other substituents using techniques well known to those skilled in the art. For example, amino may be converted to amido, amido may be hydrolysed to amino, hydroxy may be converted to alkoxy, alkoxy may be hydrolysed to hydroxy etc.

It will be appreciated by those skilled in the art that, in the processes described above, the functional groups of intermediate compounds may be, or may need to be, protected by protecting groups.

Functional groups which it is desirable to protect thus include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl, benzyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxycarbonyl. Suitable protecting groups for carboxylic acid include $C_{1-6}$ alkyl, allyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by JWF McOmie, Plenum Press (1973), and "Protective Groups in Organic Synthesis", $3^{rd}$ edition, TW Greene & PGM Wutz, Wiley-Interscience (1999).

Persons skilled in the art will appreciate that, in order to obtain compounds of formulae II, IIA or IIB in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Certain intermediates that are employed in the processes described herein are novel. According to the invention there is further provided compounds of formulae IIA, IIB, III, VI and VIIIA as defined hereinbefore.

The process of the invention possesses the advantage that sildenafil and analogues thereof may be prepared from commercially-available starting materials in fewer steps than in processes described in the prior art, without concomitant losses in terms of yield of key intermediates and of final compounds. The process of the invention has the further advantage that sildenafil and analogues thereof may be made directly from readily available intermediates described herein (i.e. compounds of formula III) in a convenient one-pot procedure.

Further, the process of the invention may have the advantage that sildenafil and analogues thereof may be prepared in less time, more conveniently, and at a lower cost, than when prepared in processes described in the prior art.

The invention is illustrated, but in no way limited, by the following examples.

All $^1$H NMR spectra were recorded using a Varian Unity 300 MHz machine.

EXAMPLE A 1-(4-Ethoxy-3-formylphenylsulfonyl)-4-methylpiperazine (a) Ethyl 2-ethoxy-5-(4-methyl-1-piperazinylsulfonyl) benzoate To a suspension of 2-ethoxy-5-(4-methyl-1-piperazinylsulfonyl)benzoic acid (16.4 g, 0.05 mol, see EP 812 845) in ethanol (160 mL) was added concentrated hydrochloric acid (12.5 mL, 0.15 mol), which gave a solution on stirring. The solution was heated to reflux for 25 hours and then allowed to cool. It was concentrated under vacuum to give an orange oil which gave crystals on cooling. These were collected by filtration to give 13.7 g of crude product, which was purified by recrystallisation in acetonitrile to give 8.1 g of product as fine white crystals (45.5%).

mp 182–183° C.

$^1$H NMR (CDCl$_3$) δ 1.39 (3H, t), 1.51 (3H, t), 2.80 (3H, s), 3.08 (2H, s), 3.17 (2H, s), 3.48 (2H, s), 3.86 (2H, s), 4.19 (2H, q), 4.38 (2H, q), 7.08 (1H, d), 7.78 (1H, d), 8.17 (1H, s)

m/z found 357 [M+H$^+$] 100%, $C_{16}H_{25}N_2SO_5$ requires 357

(b) 1-(4-Ethoxy-3-hydroxymethylphenylsulfonyl)-4-methylpiperazine

A solution of ethyl 2-ethoxy-5-(4-methyl-1-piperazinylsulfonyl)benzoate (2.0 g, 0.006 mol, from step (a) above) in toluene (40 mL) was prepared. Under a positive pressure of nitrogen, Red-Al® (4.3 mL, 0.01 mol) was transferred to a dropping funnel and added dropwise over 30 minutes. The reaction was quenched with water/THF, which was followed with a NaOH wash. DCM was added and the phases were separated. The DCM was removed in vacuo to give crude product, which was recrystallised from toluene to give the sub-title compound as yellow crystals (40.5 g, 92%).

mp 120° C.

$^1$H NMR (CDCl$_3$) δ 1.46 (3H, t), 2.23 (3H, s), 2.49 (4H, m), 3.02 (4H, m), 4.12 (2H, m), 4.69 (2H, s), 6.92 (1H, d), 7.63 (1H, d), 7.72 (1H, s)

m/z found 315 [M+H$^+$] 100%, $C_{14}H_{23}N_2O_4S$ requires 315

(c) 1-(4-Ethoxy-3-formylphenylsulfonyl)-4-methylpiperazine

MnO$_2$ (100 g, 1.15 mol) was loaded into a flask, followed by 1-(4-ethoxy-3-hydroxymethylphenylsulfonyl)-4-methylpiperazine (15 g, 0.05 mol, from step (b) above). This was washed with acetone (150 mL) and the suspension stirred for 3 hours. The MnO$_2$ was filtered off onto Celite® and the filtrate concentrated under vacuum to give a pale yellow oil. This was recrystallised from toluene to give the title compound as a pale green solid (7.4 g, 47%).

mp 107–108° C.

$^1$H NMR (CDCl$_3$) δ 1.55 (3H, t), 2.28 (3H, s), 2.47 (4H, m), 3.02 (4H, m), 4.26 (2H, q), 7.12 (1H, d), 7.93 (1H, d), 8.19 (1H, s), 10.47 (1H, s) m/z found 313 [M+H$^+$] 100%, C$_{14}$H$_{21}$N$_2$O$_4$S requires 313

The title compound was also prepared analogously to the methods described in DE 24 44 720.

EXAMPLE 1

5-[2-Ethoxy-5-(4-methylpiperazin-1-ylsulfonyl)phenyl]-1-methyl-3-n-propyl-1,6-dihydro-7H-pyrazolo[4,3-d]pyrimidin-7-one (Sildenafil)

A solution of xylene (60 mL) containing 1-(4-ethoxy-3-formylphenylsulfonyl)-4-methylpiperazine (4.0 g, 0.013 mol, prepared analogously to the methods described in DE 24 44 720) and 4-amino-1-methyl-3-propyl-1H-pyrazole-5-carboxamide (Example 37 of EP 0463756) (2.6 g, 0.014 mol) was submitted to 46 hours at 200° C. and 34.5 kPa (5 psi). The reaction was allowed to cool and the catalyst (10% Pd/C, 3.1 g, 50% w/w) was added. The reaction was heated at 200° C. under 34.5 kPa (5 psi) of pressure for a further 12 hours. The catalyst was recovered by filtration and the organic solvent removed in vacuo to give 4.2 g of crude product, which was purified by trituration in methyl ethyl ketone (MEK). This yielded 3.3 g (53%) of the title compound as an off-white solid.

mp 184–185° C.

$^1$H NMR (CDCl$_3$) δ 0.98 (3H, t), 1.62 (3H, t), 1.86 (2H, m), 2.27 (3H, s), 2.47 (4H, m), 2.94 (2H, t), 3.09 (4H, m), 4.25 (3H, s), 4.27 (2H, q), 7.17 (1H, d), 7.80 (1H, d), 8.68 (1H, s)

m/z found 475 [M+H$^+$] 100%, C$_{22}$H$_{31}$N$_6$O$_4$S requires 475

According to a highly preferred aspect of the present invention there is provided a process for the preparation of sildenafil as defined herein and in particular according to Example 1 by the reaction of 1-(4-ethoxy-3-formylphenylsulfonyl)-4-methylpiperazine and 4-amino-1-methyl-3-propyl-1H-pyrazole-5-carboxamide at elevated temperature and pressure, optionally in an appropriate solvent. In a preferred aspect said reaction is performed at 200° C. and 34.5 kPa (5 psi) for up to about 46 hours. In a further preferred aspect the reaction mixture is further treated with a suitable catalyst under elevated temperature and pressure conditions. In a yet further preferred aspect such further treatment comprises the addition of 10% Pd/C and heating at 200° C. under 34.5 kPa (5 psi) of pressure for up to about a further 12 hours in xylene.

EXAMPLE 2

4-{6-Ethoxy-5-[3-ethyl-6,7-dihydro-7-oxo-2-(2-pyridylmethyl)-2H-pyrazolo[4,3-d]pyrimidin-5-yl]-3-pyridinylsulfonyl}-1-ethylpiperazine (a) 1-(6-Ethoxy-5-formyl-3-pyridylsulfonyl)-4-ethylpiperazine DIBAL-H (14.8 mL) was added dropwise to a solution of ethyl 2-ethoxy-5-(4-ethyl-1-piperazinylsulfonyl)nicotinate (5.0 g, 13.5 mmol; prepared as described in WO 99/54333) in toluene (100 mL) at −78° C. under nitrogen. The mixture was held at −78° C. for 1 hour and then water (20 mL) was added dropwise. The mixture was allowed to warm to room temperature and then water (200 mL) and ethyl acetate (200 mL) were added. The organic layer was separated and the aqueous phase re-extracted. The combined organics were washed with brine and concentrated under vacuum to give the product as a brown oil (1.64 g, 36%).

$^1$H NMR (CDCl$_3$) δ 1.26 (3H, t), 1.47 (3H, t), 2.52 (4H, m), 3.06 (4H, m), 4.09 (2H, m), 4.59 (2H, m), 8.35 (1H, d), 8.70 (1H, d), 10.35 (1H, s)

(b) 4-{6-Ethoxy-5-[3-ethyl-4,5,6,7-tetrahydro-7-oxo-2-(2-pyridylmethyl)-2H-pyrazolo[4,3-d]pyrimidin-5-yl]-3-pyridinylsulfonyl}-1-ethylpiperazine A solution of 1-(6-ethoxy-5-formyl-3-pyridylsulfonyl)-4-ethylpiperazine (1.1 g, 4.9 mmol, from step (a) above) and 4-amino-5-ethyl-1-(2-pyridylmethyl)-1H-pyrazole-3-carboxamide (1.2 g, 4.9 mmol) in toluene (10 mL) was heated to reflux for 4 hours and the solution was concentrated under vacuum. The resulting product was recrystallised from ethyl acetate to give a pale brown solid (1.4 g, 52%).

$^1$H NMR (CDCl$_3$) δ 1.02 (3H, t), 1.14 (3H, t), 1.45 (3H, t), 2.40 (2H, m), 2.52 (4H, m), 2.78 (2H, m), 3.09 (4H, m), 4.55 (2H, m), 5.40 (2H, s), 7.01 (1H, d), 7.23 (1H, m), 7.65 (2H, m), 8.56 (3H, m), 9.25 (1H, s).

(c) 4-{6-Ethoxy-5-[3-ethyl-6,7-dihydro-7-oxo-2-(2-pyridylmethyl)-2H-pyrazolo[4.3-d]pyrimidin-5-yl]-3-pyridinylsulfonyl}-1-ethylpiperazine To a solution of 4-{6-ethoxy-5-[3-ethyl-4,5,6,7-tetrahydro-7-oxo-2-(2-pyridylmethyl)-2H-pyrazolo[4,3-d]pyrimidin-5-yl]-3-pyridinylsulfonyl}-1-ethylpiperazine (50 mg, 0.09 mmol, from step (b) above) in toluene (1 mL), was added 10% Pd/C (25 mg, 50% w/w) and trifluoroacetic acid (14 μL). The mixture was heated to 200° C. under nitrogen at 34.5 kPa (5 psi) for 6 hours. The resulting mixture was filtered and concentrated in vacuo to a pale yellow oil. This was dissolved in DCM (5 mL) and washed with NaHCO$_3$ (2 mL), dried over MgSO$_4$ and concentrated to give a brown oil (42 mg, 84%) as product.

$^1$H NMR (CDCl$_3$) δ 1.02 (3H, t), 1.30 (3H, t), 1.58 (3H, t), 2.41 (2H, q), 2.55 (4H, m), 3.04 (2H, q), 3.10 (4H, m), 4.75, (2H, q), 5.69 (2H, s), 7.10 (1H, d), 7.22 (1H, m), 7.63 (1H, m), 8.57 (1H, d), 8.63 (1H, d), 9.02 (1H, d).

Preparation 1

2-Ethyl-2-ethoxy-5-(4-ethyl-1-piperazinylsulfonyl) pyridinoate—Compound VIIIB (1a) 2-Hydroxy-5-sulfonicotinic Acid 2-Hydroxynicotinic acid (27 Kg, 194.2 mol) was added portionwise to 30% oleum (58.1 Kg) at 50° C. over 1 hr. This caused an exotherm to 82° C. The reaction mixture was heated further to 140° C. After maintaining this temperature for 12 hrs the reactor contents were cooled to 15 C and filtered. The filter cake was then re-slurried with acetone (33 Kg) at room temperature, filtered and dried to afford the title compound (35.3 Kg, 83%) as a white solid. Decomposition pt 273° C. δ (DMSO$_{d6}$): 7.93 (1H, d), 8.42 (1H, d). m/z (Found:220 [M+H]$^+$, 100%. C$_6$H$_6$NO$_6$S requires 220.17).

(1b) Ethyl 2-hydroxy-5-sulfonicotinoate

2-Hydroxy-5-sulfonicotinic acid (500 g, 2.28 mol) was dissolved in ethanol (2.5 L) with stirring and heated to 80° C. After 30 mins 0.5 L of solvent was distilled off, then replaced with fresh ethanol (0.5 L) and taken back to 80° C. After a further 60 mins 1.0 L of solvent was distilled off, then replaced with fresh ethanol (1.0 L) and taken back to 80° C. After a further 60 mins 1.0 L of solvent was distilled off, the reaction cooled to 22° C. and stirred for 16 hr. The precipitated product was filtered, washed with ethanol (0.5 L) and dried at 50° C. under vacuum to afford the title compound (416 g, 74%) as a white solid. Decomposition pt 237° C. δ (DMSO$_{d6}$): 1.25 (3H, t), 4.19 (2H, q), 7.66 (1H, d), 8.13 (1H, d). m/z (Found:248 [M+H]+, 100%. $C_8H_{10}NO_6S$ requires 248.22).

(1c) Ethyl 2-chloro-5-chlorosulfonicotinoate

Ethyl 2-hydroxy-5-sulfonicotinoate (24.7 g, 0.1 mol) was slurried in thionyl chloride (238 g, 2.0 mol) and dimethylformamide (1.0 mL) with stirring. The reaction mixture was then heated to reflux for 2.5 hr. The bulk of the thionyl chloride was removed under vacuum with residual thionyl chloride removed with a toluene azeotrope to afford the crude title compound (30.7 g, 108%) as a yellow oil. δ (CDCl$_3$): 1.46 (3H, t), 4.50 (2H, q), 8.72 (1H, d), 9.09 (1H, d). This was taken directly onto the next step.

(1d) Ethyl 2-chloro-5-(4-ethyl-1-piperazinylsulfonyl) nicotinoate

Crude ethyl 2-chloro-5-chlorosulfonicotinoate (30.7 g, 0.1 mol assumed) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (50 mL), carefully over 30 mins, keeping the internal temperature below 10° C. Once the addition was complete the reaction was allowed to warm to 22° C. and stir for 1 hr. The solid was filtered off and the remaining filtrate was concentrated under vacuum to afford the crude title compound (37.1 g, 103%) as a crude yellow gum. δ (CDCl$_3$): 1.10 (3H, t), 1.42 (3H, m), 2.50 (2H, m), 2.60 (4H, m), 3.19 (4H, m), 4.43 (2H, q), 8.40 (1H, d), 8.80 (1H, d). m/z (Found:362 [M+H]+, 100%. $C_{14}H_{21}ClN_3O_4S$ requires 362.85).

(1e) Ethyl 2-ethoxy-5-(4-ethyl-1-piperazinylsulfonyl) nicotinoate

A solution of ethyl 2-chloro-5-(4-ethyl-1-piperazinylsulfonyl)nicotinoate (36.1 g, 0.1 mol) in ethanol (180 mL) was cooled to 10° C. with stirring. Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the title compound (12.6 g, 34%) as a light brown solid. M.p. 66–68° C. δ (CDCl$_3$): 1.04 (3H, t), 1.39 (3H, t), 1.45 (3H, t), 2.41 (2H, q), 2.52 (4H, m), 3.08 (4H, m), 4.38 (2H, q), 2.57 (2H, q), 8.38 (1H, d), 8.61 (1H, d). m/z (Found: 372 [M+H]+, 100%. $C_{16}H_{26}N_3O_5S$ requires 372.46).

(1f) 2-Ethoxy-5-(4-ethyl-1-piperazinylsulfonyl)nicotinic Acid

Ethyl 2-ethoxy-5-(4-ethyl-1-piperazinylsulfonyl) nicotinoate (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH=5.6 by addition of conc. hydrochloric acid. The precipitated product was slurried with ice cooling for 15 minutes, filtered, water washed and dried under vacuo at 50° C. to afford the title compound (4.1 g, 43%) as an off-white solid. Mpt 206–207° C. δ (CDCl$_3$): 1.25 (3H, t), 1.39 (3H, t), (2H, q), 3.03 (4H, m), 3.25 (4H, m), 4.50 (2H, q), 8.25 (1H, d), 8.56 (1H, d). m/z (Found:344 [M+H]+, 100%. $C_{14}H_{22}N_3O_5S$ requires 344.38).

This step is a simple hydrolysis and the yield of 43% is not optimum. The same hydrolysis was carried out in preparation 23 of PCT/IB99/00519 (which is incorporated herein by reference) and a more optimised yield of 88% was obtained for the hydrolysis.

Preparation 2
2-Ethoxy-5-(4-ethyl-1-piperazinylsulfonyl)nicotinic Acid—Telescoped Process in Toluene from Ethyl 2-hydroxy-5-sulfonicotinoate Ethyl 2-hydroxy-5-sulfonicotinoate (441.5 g, 1.79 mol) was dissolved in toluene (1.77 L) and thionyl chloride (1.06 Kg, 8.93 mol) and dimethylformamide (71.3 mL) were then added. The stirred suspension was then heated to reflux for 3 hours to yield a yellow solution. Thionyl chloride (2.87 L) was then distilled with continual replacement with toluene (2.15 L). The pale yellow solution was then cooled to 10° C. and a stirred solution of N-ethylpiperazine (198.9 g, 1.66 mol) and triethylamine (392.2 g, 3.88 mol) in toluene (700 mL) added dropwise over 90 minutes keeping the reaction mixture below 10° C. The reaction was stirred at ambient temperature for 18 hours then washed with water (2×700 mL) and brine (2×350 mL). The toluene phase was azeotropically dried by distilling off 1750 mL which was continuously replaced by dry toluene (1750 mL). The remaining brown solution was cooled to 10° C. and sodium ethoxide (178.0 g, 2.62 mol) was added portionwise keeping the temperature below 10° C. The reaction was then stirred at 10° C. for 1 hour then allowed to warm to ambient temperature and stirred for 18 hours. Sodium hydroxide (34.9 g, *mol) dissolved in water (1.5 L) was then added to the toluene mixture and the 2 phase mixture was vigorously stirred for 18 hours at 40° C. Once cooled to ambient temperature the aqueous phase was separated off. To this was added conc. hydrochloric acid to pH=3 which precipitated a light brown solid which was granulated for 2 hour with ice cooling. The precipitate was filtered washed with water (300 mL) and dried under vacuo at 50° C. to afford the title compound (338.4 g, 57.4%) as an off-white solid. Mpt 206–207° C. δ (CDCl$_3$): 1.25 (3H, t), 1.39 (3H, t), 2.82 (2H, q), 3.03 (4H, m), 3.25 (4H, m), 4.50 (2H, q), 8.25 (1H, d), 8.56 (1H, d). m/z (Found:344 [M+H]+, 100%. $C_{14}H_{22}N_3O_5S$ requires 344.38).

Preparations 3 and 4 provide alternative routes by which two of the additional compounds can be prepared.

Preparation 3
2-(Methoxyethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

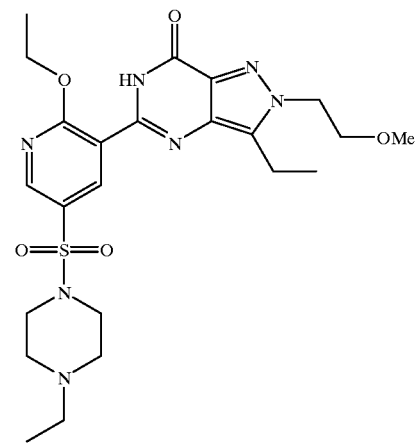

A mixture of the product from stage i) below (0.75 mmol), potassium bis(trimethylsilyl)amide (298 mg, 1.50 mmol) and ethyl acetate (73 microliters, 0.75 mmol) in ethanol (10 ml) was heated at 120° C. in a sealed vessel for 12 hours.

The cooled mixture was partitioned between ethyl acetate and aqueous sodium bicarbonate solution, and the layers separated. The organic phase was dried (MgSO$_4$), and evaporated under reduced pressure. The crude product was purified by column chromatography on silica gel using dichloromethane:methanol (98:2) as eluant to afford the title compound, 164 mg; Found: C, 53.18; H, 6.48; N, 18.14; C$_{23}$H$_{33}$N$_7$O$_5$S; 0.20C$_2$H$_5$CO$_2$CH$_3$ requires C, 53.21; H, 6.49; N, 18.25%; δ (CDCl$_3$): 1.04 (3H, t), 1.40 (3H, t), 1.58 (3H, t), 2.41 (2H, q), 2.57 (4H, m), 3.08 (2H, q), 3.14 (4H, m), 3.30 (3H, s), 3.92 (2H, t), 4.46 (2H, t), 4.75 (2H, q), 8.62 (1H, d), 9.04 (1H, d), 10.61 (1H, s); LRMS: m/z 520 (M+1)$^+$; mp 161–162° C.

Preparation of Starting Materials for Example 1 a) Pyridine-2-amino-5-sulphonic Acid

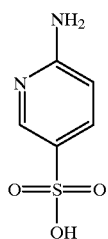

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound as a solid, 111.3 g; LRMS: m/z 175 (M+1)$^+$.

b) Pyridine-2-amino-3-bromo-5-sulphonic Acid

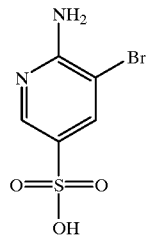

Bromine (99 g, 0.62 mol) was added dropwise over an hour, to a hot solution of the product from stage a) (108 g, 0.62 mol) in water (600 ml) so as to maintain a steady reflux. Once the addition was complete the reaction was cooled and the resulting mixture filtered. The solid was washed with water and dried under suction to afford the title compound, 53.4 g; δ (DMSOd$_6$, 300 MHz): 8.08 (1H, s), 8.14 (1H, s); LRMS: m/z 253 (M)$^+$.

c) Pyridine-3-bromo-2-chloro-5-sulphonyl Chloride

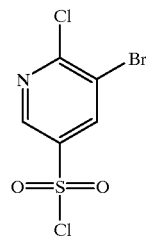

A solution of sodium nitrite (7.6 g, 110.0 mmol) in water (30 ml) was added dropwise to an ice-cooled solution of the product from stage b) (25.3 g, 100.0 mmol) in aqueous hydrochloric acid (115 ml, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144 mmol) and phosphorus oxychloride (1 ml, 10.8 mmol) was heated at 125° C. for 3 hours, and then cooled. The reaction mixture was poured onto ice (100 g) and the resulting solid filtered, and washed with water. The product was dissolved in dichloromethane, dried (MgSO$_4$), and evaporated under reduced pressure to afford the title compound as a yellow solid, 26.58 g; δ (CDCl$_3$, 300 MHz): 8.46 (1H, s), 8.92 (1H, s).

d) 3-Bromo-2-chloro-5-(4-ethylpiperazin-1-ylsulphonyl) pyridine

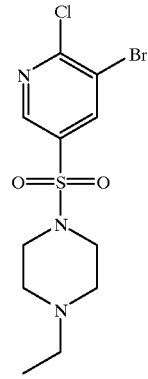

A solution of 1-ethylpiperazine (11.3 ml, 89.0 mmol) and triethylamine (12.5 ml, 89.0 mmol) in dichloromethane (150 ml) was added dropwise to an ice-cooled solution of the product from stage c) (23.0 g, 79.0 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid, 14.5 g; δ (CDCl$_3$, 300 MHz): 1.05 (3H, t), 2.42 (2H, q), 2.55 (4H, m), 3.12 (4H, m), 8.24 (1H, s), 8.67 (1H, s).

e) 3-Bromo-2-ethoxy-5-(4-ethylpiperazin-1-ylsulphonyl) pyridine

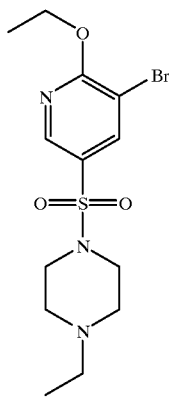

A mixture of the product from stage d) (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried (MgSO$_4$) and evaporated under reduced pressure to afford the title compound as a brown solid, 6.41 g; Found C, 41.27; H, 5.33; N, 11.11. $C_{13}H_{20}BrN_3O_3S$ requires C, 41.35; H, 5.28; N, 10.99%; δ (CDCl$_3$, 300 MHz) 1.06 (3H, t), 1.48 (3H, t), 2.42 (2H, q), 2.56 (4H, m), 3.09 (4H, m), 4.54 (2H, q), 8.10 (1H, s), 8.46 (1H, s); LRMS: m/z 378, 380 (M+1)$^+$.

f) Pyridine 2-ethoxy-5-(4-ethylpiperazin-1-ylsulphonyl)-3-carboxylic Acid Ethyl Ester

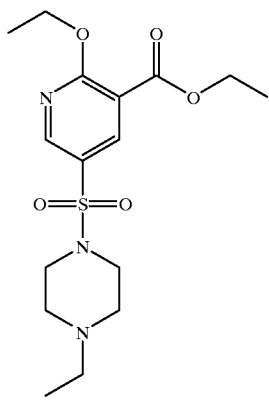

A mixture of the product from stage e) (6.40 g, 16.92 mmol), triethylamine (12 ml, 86.1 mmol), and palladium (O) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound as an orange oil, 6.2 g; δ (CDCl$_3$, 300 MHz): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s); LRMS: m/z 372 (M+1)$^+$.

g) Pyridine 2-ethoxy-5-(4-ethylpiperazin-1-ylsulphonyl)-3-carboxylic Acid

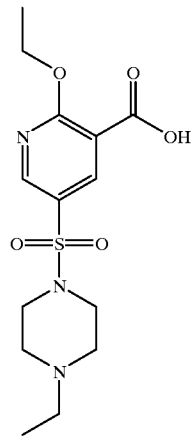

A mixture of the product from stage f) (4.96 g, 13.35 mmol) and aqueous sodium hydroxide solution (25 ml, 2N, 50.0 mmol) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried (MgSO$_4$) and evaporated under reduced pressure to afford the title compound as a tan coloured solid, 4.02 g; δ (DMSOd$_6$, 300 MHz): 1.18 (3H, t), 1.37 (3H, t), 3.08 (2H, q), 3.17–3.35 (8H, m), 4.52 (2H, q), 8.30 (1H, s), 8.70 (1H, s).

h) 4-[2-Ethoxy-5-(4-ethylpiperazin-1-ylsulphonyl)pyridin-3-ylcarboxamido]-1H-3-ethylpyrazole-5-carboxamide

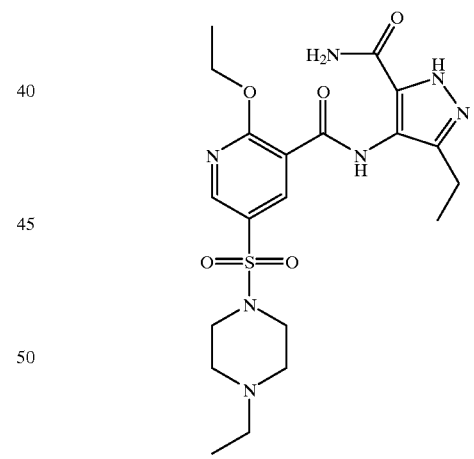

A solution of 4-amino-3-ethyl-1H-pyrazole-5-carboxamide (WO 9849166, preparation 8) (9.2 g, 59.8 mmol) in N,N-dimethylformamide (60 ml) was added to a solution of the product from stage g) (21.7 g, 62.9 mmol), 1-hydroxybenzotriazole hydrate (10.1 g, 66.0 mmol) and triethylamine (13.15 ml, 94.3 mmol) in dichloromethane (240 ml). 1-(3-Dimethylaminopropyl)-3-ethylcarbodiimide hydrochloride (13.26 g, 69.2 mmol) was added and the reaction stirred at room temperature for 6 hours. The dichloromethane was removed under reduced pressure, the remaining solution poured into ethyl acetate (400 ml), and this mixture washed with aqueous sodium bicarbonate solution (400 ml). The resulting crystalline precipitate was filtered, washed with ethyl acetate and dried under vacuum, to afford the title compound, as a white powder, 22 g; δ (CDCl$_3$+1 drop DMSOd$_6$) 0.96 (3H, t), 1.18 (3H, t), 1.50 (3H, t), 2.25–2.56 (6H, m), 2.84 (2H, q), 3.00 (4H, m), 4.70 (2H, q), 5.60 (1H, br s), 6.78 (1H, br s), 8.56 (1H, d), 8.76 (1H, d), 10.59 (1H, s), 12.10–12.30 (1H, s); LRMS: m/z 480 (M+1)$^+$.

i) 2-Methoxyethyl-4-[2-ethoxy-5-(4-ethylpiperazin-1-ylsulphonyl)pyridin-3-ylcarboxamido]-3-ethylpyrazole-5-carboxamide

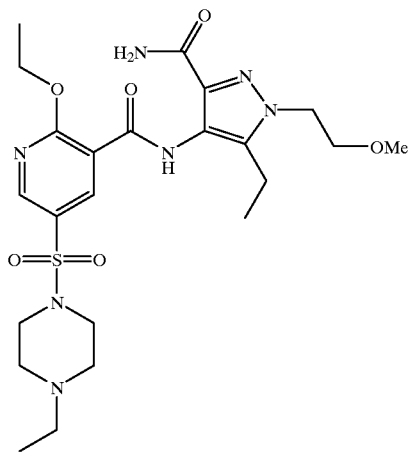

1-Bromo-2-methoxyethane (1.72 mmol) was added to a solution of the product from stage h) (750 mg, 1.56 mmol) and caesium carbonate (1.12 g, 3.44 mmol) in N,N-dimethylformamide (15 ml) and the reaction stirred at 60° C. for 18 hours. The cooled mixture was partitioned between water and ethyl acetate, and the layers separated. The organic layer was dried (MgSO$_4$), concentrated under reduced pressure and azeotroped with toluene to give a solid. This product was recrystallised from ether, to afford the title compound as a white solid.

What is claimed is:
1. A process for the production of a compound of general formula I:

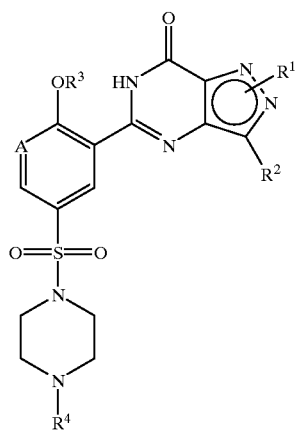

wherein
A represents CH or N;
R$^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, OR$^5$, C(O)R$^6$, C(O)OR$^7$, C(O)NR$^8$R$^9$, NR$^{10a}$R$^{10b}$ and SO$_2$NR$^{11a}$R$^{11b}$
R$^2$ and R$^4$ independently represent lower alkyl;
R$^3$ represents lower alkyl, which alkyl group is optionally interrupted by oxygen;
Het represents an optionally substituted four- to twelve-membered heterocyclic group, which group contains one or more heteroatoms selected from nitrogen, oxygen and sulfur;
R$^5$, R$^6$, R$^7$, R$^8$, R$^9$, R$^{11a}$ and R$^{11b}$ independently represent H or lower alkyl;
R$^{10a}$ and R$^{10b}$ either independently represent, H or lower alkyl or, together with the nitrogen atom to which they are attached, represent azetidinyl, pyrollidinyl or piperidinyl, which process comprises the dehydrogenation of a compound of general formula II,

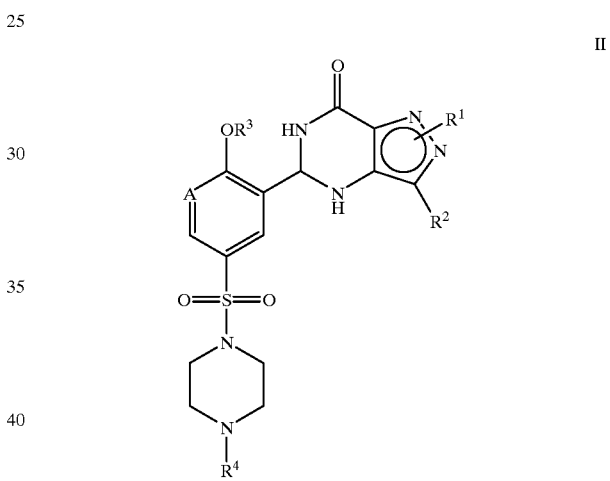

wherein A, R$^1$, R$^2$, R$^3$ and R$^4$ are as defined above;
said dehydrogenation being carried out in the presence of a dehydrogenation agent selected from: palladium on carbon; palladium on carbon in the presence of a hydrogen acceptor and/or an acid; a high oxidation potential quinone; oxygen; MnO$_2$; or triphenylmethanol in trifluoroacetic acid.

2. A process as claimed in claim 1, wherein, in the compound of general formula I, R$^1$ represents C$_{1-4}$ alkyl, which alkyl group is optionally interrupted by an oxygen atom, and/or is optionally terminated by a Het group.

3. A process as claimed in claim 2, wherein R$^1$ represents linear C$_{1-3}$ alkyl, which alkyl group is optionally interrupted by an oxygen atom, or is optionally terminated by a 2-pyridinyl group.

4. A process as claimed in claim 1, wherein, in the compound of general formula I, R$^2$ represents C$_{1-4}$ alkyl.

5. A process as claimed in claim 4, wherein R$^2$ represents linear C$_{2-3}$ alkyl.

6. A process as claimed in claim 1, wherein, in the compound of general formula I, R$^3$ represents C$_{1-5}$ alkyl, which alkyl group is optionally interrupted by an oxygen atom.

7. A process as claimed is claim 6, wherein $R^3$ represents linear or branched $C_{2-4}$ alkyl, which alkyl group is optionally interrupted by an oxygen atom.

8. A process as claimed in claim 1, wherein, in the compound of general formula I, $R^4$ represents $C_{1-3}$ alkyl.

9. A process as claimed in claim 8, wherein $R^4$ represents $C_{1-2}$ alkyl.

10. A process as claimed in claim 1, wherein the compound is selected from sildenafil, or any one of the following four compounds

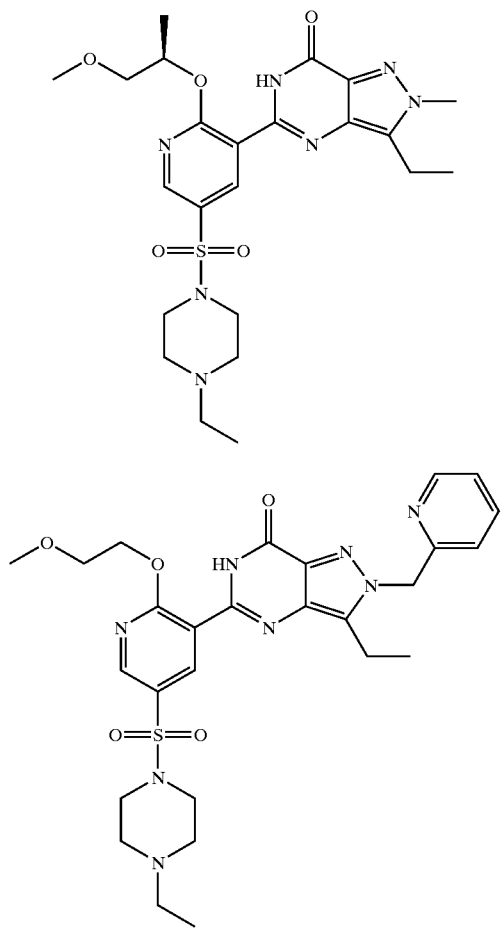

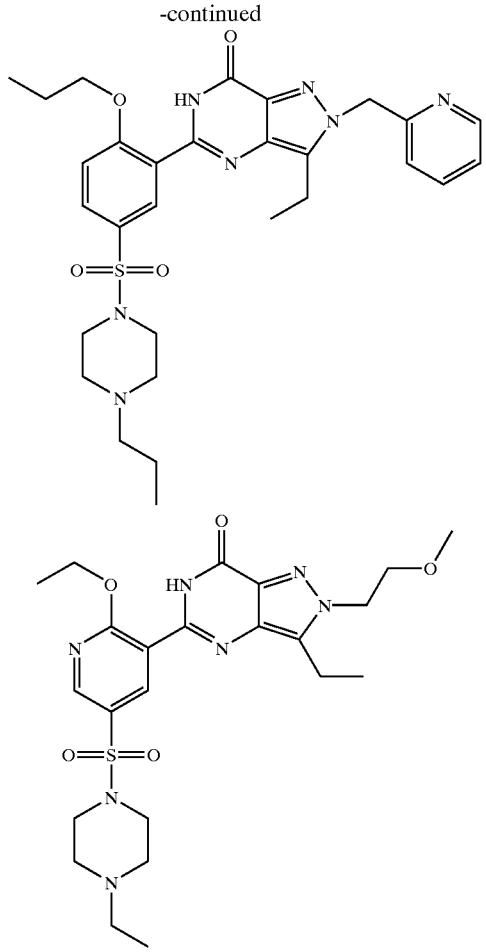

11. A process as claimed in claim 1, wherein the palladium on carbon is 5% Pd/C or 10% Pd/C.

12. A process as claimed in claim 1, wherein the hydrogen acceptor is cyclohexene or maleic acid.

13. A process as claimed in claim 1, wherein the acid is trifluoroacetic acid, HCl or $H_2SO_4$.

14. A process as claimed in claim 1, wherein the reaction is carried out in the presence of an aromatic hydrocarbon as solvent.

15. A process as claimed in claim 14, wherein the solvent is toluene or xylene.

16. A process as claimed in claim 1, wherein the reaction is carried out at between 125 and 250° C., at a pressure of between 13.8 and 68.9 kPa (2 and 10 psi), and/or, optionally, in an inert atmosphere.

* * * * *